(12) United States Patent
Martin et al.

(10) Patent No.: US 9,001,331 B2
(45) Date of Patent: Apr. 7, 2015

(54) ARRANGEMENT ADAPTED FOR SPECTRAL ANALYSIS OF HIGH CONCENTRATIONS OF GAS

(75) Inventors: Hans Göran Evald Martin, Delsbo (SE); Pavel Zyrianov, Delsbo (SE)

(73) Assignee: Senseair AB, Delsbo (SE)

( * ) Notice: Subject to any disclaimer, the term of this patent is extended or adjusted under 35 U.S.C. 154(b) by 894 days.

(21) Appl. No.: 13/121,485

(22) PCT Filed: Sep. 24, 2009

(86) PCT No.: PCT/SE2009/051064
§ 371 (c)(1),
(2), (4) Date: May 26, 2011

(87) PCT Pub. No.: WO2010/039091
PCT Pub. Date: Apr. 8, 2010

(65) Prior Publication Data
US 2011/0235042 A1 Sep. 29, 2011

(30) Foreign Application Priority Data

Sep. 30, 2008 (SE) ...................................... 0802069

(51) Int. Cl.
*G01N 21/00* (2006.01)
*G01N 21/3504* (2014.01)
*G01N 21/03* (2006.01)
(52) U.S. Cl.
CPC ........ *G01N 21/3504* (2013.01); *G01N 21/0303* (2013.01)

(58) Field of Classification Search
CPC ........................ G01N 21/3504; G01N 21/0303
USPC .................................................... 356/436–437
See application file for complete search history.

(56) References Cited

U.S. PATENT DOCUMENTS

| 4,029,521 A | | 6/1977 | Korn et al. |
| 4,662,755 A | | 5/1987 | Aoki et al. |
| 4,694,173 A | * | 9/1987 | Wong .............................. 250/343 |
| 4,893,935 A | * | 1/1990 | Mandel et al. ................. 356/436 |
| 4,975,582 A | * | 12/1990 | Mount et al. ................... 250/343 |

(Continued)

FOREIGN PATENT DOCUMENTS

| DE | 41 10 653 | 1/1992 |
| EP | 0 557 655 A1 | 9/1993 |

(Continued)

*Primary Examiner* — Kara E Geisel
*Assistant Examiner* — Dominic J Bologna
(74) *Attorney, Agent, or Firm* — Drinker Biddle & Reath LLP

(57) ABSTRACT

A device adapted for spectral analysis having a transmitting means adapted for electromagnetic radiation, a delimited space, in the form of a cavity, serving as a measuring cell and intended to be capable of defining an optical measuring distance, a sensing means of the electromagnetic radiation passing the optical measuring distance from said transmitting means, and a unit at any rate connected to the sensing means performing the spectral analysis, the sensing means for the electromagnetic radiation is opto-electrically adapted sensitive to the electromagnetic radiation, which is intended to fall within the spectral range whose chosen wavelength components or spectral elements are to become objects of an analysis in the unit performing the spectral analysis for determining in this unit, over calculations, the relative intensity of radiation of the spectral element.

17 Claims, 2 Drawing Sheets

(56) References Cited

U.S. PATENT DOCUMENTS

| | | |
|---|---|---|
| 5,009,493 A | 4/1991 | Koch et al. |
| 5,054,919 A | 10/1991 | Bryan |
| 5,129,401 A | 7/1992 | Corenman et al. |
| 5,268,782 A | 12/1993 | Wenz et al. |
| 5,384,640 A * | 1/1995 | Wong .................. 356/437 |
| 5,478,750 A | 12/1995 | Bernstein et al. |
| 5,677,534 A * | 10/1997 | Araya .................. 250/345 |
| 5,747,808 A * | 5/1998 | Wong .................. 250/343 |
| 5,773,828 A | 6/1998 | Akiyama et al. |
| 6,016,203 A | 1/2000 | Martin |
| 6,194,735 B1 | 2/2001 | Martin |
| 6,372,542 B1 | 4/2002 | Martin et al. |
| 6,921,899 B2 | 7/2005 | Martin |
| 7,326,922 B1 * | 2/2008 | Mueller .................. 250/252.1 |
| 2004/0145741 A1 * | 7/2004 | Cole et al. .................. 356/436 |
| 2005/0057753 A1 * | 3/2005 | Mosley et al. .............. 356/436 |
| 2006/0119851 A1 | 6/2006 | Bounaix |
| 2008/0094632 A1 * | 4/2008 | Harsh et al. .................. 356/436 |
| 2009/0213380 A1 * | 8/2009 | Appel et al. .................. 356/437 |

FOREIGN PATENT DOCUMENTS

| | | |
|---|---|---|
| EP | 1 659 390 A1 | 5/2006 |
| GB | 1514507 A | 6/1978 |
| JP | 60214239 | 10/1985 |
| JP | S61-17651 U | 2/1986 |
| JP | 1996029346 | 2/1996 |
| WO | 97/18460 | 5/1997 |
| WO | 98/09152 | 3/1998 |
| WO | 99/41592 | 8/1999 |
| WO | 01/81901 | 11/2001 |
| WO | 2004/048929 | 6/2004 |
| WO | WO-2010024756 A1 | 3/2010 |

* cited by examiner

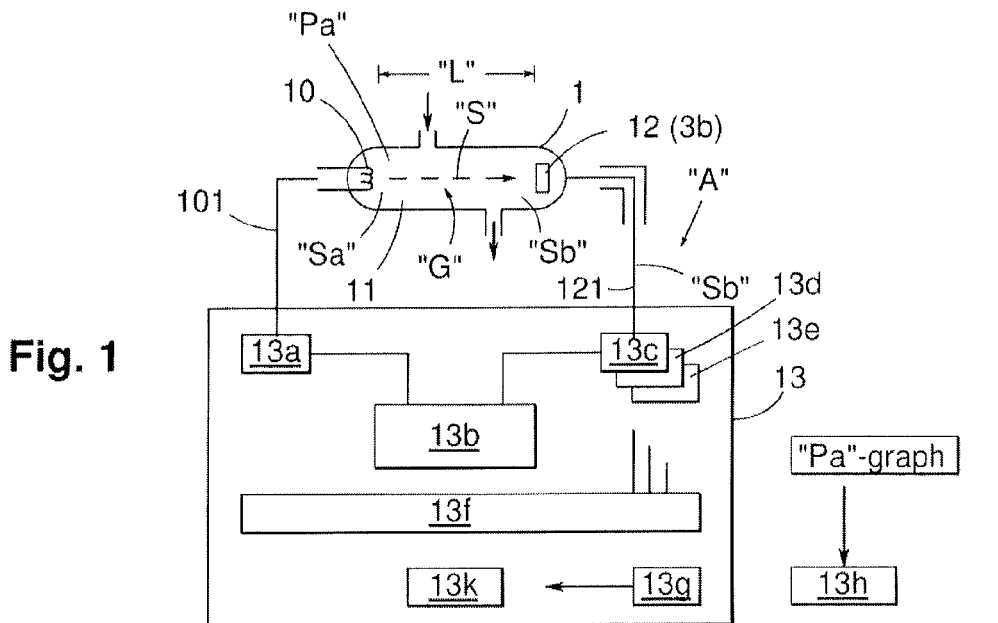
Fig. 1
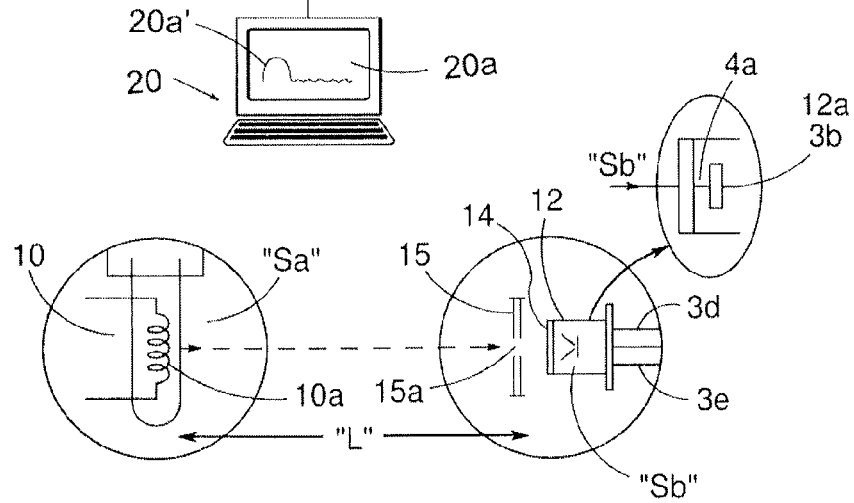
Fig. 2
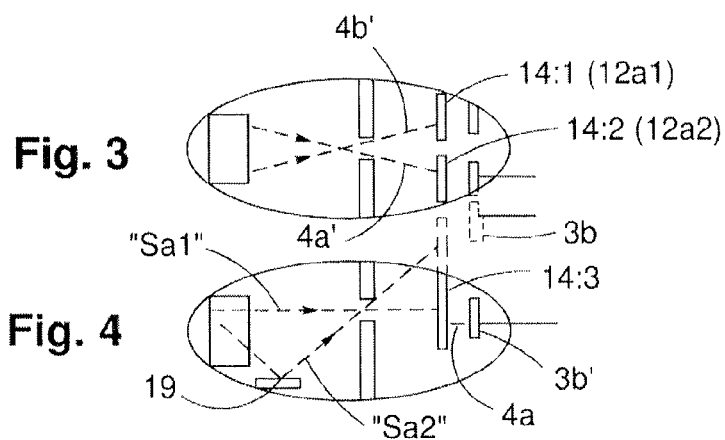
Fig. 3
Fig. 4

ARRANGEMENT ADAPTED FOR SPECTRAL ANALYSIS OF HIGH CONCENTRATIONS OF GAS

RELATED APPLICATION DATA

This application is a §371 National Stage Application of PCT International Application No. PCT/SE2009/051064 filed Sep. 24, 2009, and also claims priority under 35 U.S.C. §119 and/or §365 to Swedish Application No. 0802069-5, filed Sep. 30, 2008.

TECHNICAL FIELD OF THE INVENTION

This invention generally refers to an arrangement adapted for or to electromagnetic radiation and primarily for evaluating high concentrations of one or more gases or gas mixtures.

The practical application of the invention will be described more specifically in the following, in connection with a gas-adapted arrangement or a gas meter for being able to determine the existence of gas by means of this gas meter, said gas at that time occurring in the form of relatively high concentrations of gas or gas mixtures in a sample of gas adapted for evaluation and being enclosed in or passing through a measuring cell.

Such gas-adapted arrangement is then to exhibit an emitting or transmitting means, adapted for electromagnetic radiation, and having a cavity serving as a measuring cell for a sample of gas and intended to be able to define an optical measuring distance applicable to the measuring itself, a detecting or sensing means or detector of said electromagnetic radiation passing through said optical measuring distance from said transmitting means, and a unit performing spectral analysis and being connected in any case to said sensing means or detector.

Said means sensing or detecting the electromagnetic radiation is adaptedly opto-electrically sensitive to the electromagnetic radiation which is intended to fall within the spectral field whose chosen wavelength component(s) or spectral element(s) is/are to become the object of an analysis within the unit performing the spectral analysis so as to determine in this unit the relative intensity of radiation of the spectral element.

In this technical field the transmitting means and sensing means or detector indicated and utilized here are known in the prior art as well as units performing spectral analyses and thereto connected display units or similar presenting the results, and therefore these means, units and display units will not be the object of the more specific penetration and illustration in this application with regard to their structural composition.

BACKGROUND OF THE INVENTION

Methods, arrangements and structures related to the technical field and character mentioned above are known earlier in a plurality of different embodiments.

As a first example of the technical background and the technical field to which the invention refers may be mentioned an arrangement adapted for spectral analysis of a sample of a gas and/or a gas mixture with a transmitting means adapted for electromagnetic radiation, a space, such as a delimited space in the form of a cavity, serving as a measuring cell and intended to be able to define an optical measuring distance, a sensing or detecting means for said electromagnetic radiation passing said optical measuring distance from said transmitting means, and at least one, to said sensing means related one or more opto-electric detectors with associated light-receiving and/or light-sensitive portions, such as chips, connected unit performing a spectral analysis of the sample of gas.

Said means, sensing the electromagnetic radiation, is opto-electrically adaptedly sensitive to the electromagnetic radiation, which is intended to fall within the spectral field whose chosen wavelength components or spectral elements are to become objects of an analysis in said unit performing the spectral analysis for determining in this unit the relative radiation intensity of the spectral element(s) for relevant and chosen wavelength portions.

Reference is here made to U.S. Pat. No. 5,009,493, German Patent Publication DE-A1-4 110 653, U.S. Pat. Nos. 5,268,782 and 4,029,521.

As a more specific first example of the arrangement analysing the sample of gas indicated here, reference is made to the contents of the published International Patent Application No. PCT/SE99/00145 (WO 99/41 592-A1), comprising a method for producing a detector related to a gas sensor and a detector thus produced.

As a second, more specific example of the arrangement indicated here, reference is made to the published International Patent Application having Publication No. WO 97/18460-A1.

As a third specific example of the arrangement indicated here, reference is made to the contents of the published International Patent Application having Publication No. WO 98/09152 A1.

Furthermore, reference is made to the contents of the International Patent Application having Publication No. WO 01/81 901 A1.

With regard to the peculiarities related to the present invention it may be mentioned that it is also known that the relative intensity of radiation of a spectral element(s) for relevant wavelength sections is low in lesser and very small concentrations of gas and that the achieved results have turned out to exhibit large margins of error.

In known units for spectral analyses normally a minimum (high) concentration of gas is required on the one hand for determining the relevant gas and on the other hand for evaluating the relevant concentration of gas therein.

It is known to supply, at right angles to a bandpass filter, electromagnetic or optical radiation having a large wave range and to create in the filter prerequisites for letting through a selected narrow wave range to an opto-electric detector so as to have in this detector, with its light-receiving and light-sensitive portion, such as a chip, and a unit connected thereto for performing spectral analysis, the intensity and/or relative intensity of the narrow wave range evaluated.

Generally, in gas test analyses over a spectral analysis of chosen wave range, it is known that different criteria provide different measuring results with varying accuracy.

Thus it is earlier known:
a. that a chosen furnished high power to the transmitting means normally increases the accuracy of the measuring result,
b. while utilizing pulse technology the transmitting means can be activated periodically in order to create prerequisites for permitting the chip of the detector to cool off between activating pulses,
c. with an increasing measuring distance through a sample of gas, between the transmitting means and the chip of the detector, to increase the exactness of the measuring result, applicable in low concentrations,
d. that different gases in a sample of gas provide different significative absorption spectra at different frequencies and/or frequency sections, e. that different gases in a sample of gas provide a plurality of significative absorption spectra, at different frequencies and/or frequency sections,
f. that a sample of gas, placed under an overpressure, can, corrected to the atmospheric pressure, increase the accuracy of the result of the measuring,
g. that more and more sophisticated measuring units can be made to provide a more exact measuring result, and
h. that for one and the same concentration of gas there is an optimized measuring distance.

Considering the prerequisites of the present invention and the measuring distance assigned and utilized at that time, it is known in the prior art that very short measuring distances can have the disadvantage and expose of the following drawbacks:
  i. that heat energy transferred from the transmitting means to a chip of the detector causes annoying background light and/or background noise and heat, which reduces the accuracy of the result of the measuring,
  j. to reduce the heating of the detector and its chip, by leading generated heat into the material of the measuring cell, to the greatest possible extent,
  k. to reduce the effect of conditions, to the greatest possible extent, by synchronous detection so as to clarify the influence of the transmitter in the response of the detector,
  l. to create prerequisites for subtracting noise from a detected signal in the detector and its chip to the greatest possible extent,
  m. to create good mechanical prerequisites for effective cooling of the detector and its chips,
  m. to create prerequisites for additionally reducing the influence of radiated heat to the detector, such as by leading heat over the sample of gas, in the cavity of the measuring cell.

Considering the significant features related to the present invention the following prior art publications are to be mentioned.

The European Patent Publication EP-1 659 390-A1 is related to a microchip testing device (10), having an absorbance measuring chamber (25) for measuring absorbances, a transmitted light receiving unit (15) for receiving light, which has been emitted from the light source (13) and have been transmitted through the absorbance measuring chamber (25), an aperture, which extends in a straight line in the direction of an optical axis of the absorbance measuring chamber, with an entry opening for the light emitted by the light source on one end and a light exit opening on an opposite end, from which the light enters the absorbence measuring chamber, an incident light beam splitter, which is located in the optical path between the light exit opening of the aperture and the absorbance measuring chamber and which transmits a first part of the incident light and reflects another part of it, and a reflected light receiving part, for receiving the light which has been reflected by the beam splitter.

The arrangement thus described is adapted to test a liquid, and especially evaluating blood tests.

Patent Publication WO 2004/048 929-A2 is describing a high throughput screening with parallel vibrational spectroscopy.

It is shown and described a device and a method for a rapid spectrum assay of multiple samples with infrared light that may increase total light throughput.

Multiple wavelengths scan with Fouriee analysis is here combined with large numbers of sample wells located within infrared light compatible solid materials.

Very large scale measurement devices and systems for their use are fabricated from lithography and other techniques used for semiconductor processing.

FIG. 1 of Patent Publication WO 2004/084 929-A2 is showing that light from a light source (105) passes through a beam splitter (110) and is reflected by interferometer mirrors (115) into spectral filter (120).

Light from spectral filter (120) is focused via focusing and beam steering optics (125) into a bottom of a sample holder (130).

The light than interacts with each sample in one or more passes and is than reflected out of the sample holder (130) and is focused by optics (135) into an infrared camera (140).

An embodiment of this system comprises five components; 1), source of infrared radiations, 2), a device to modulate the radiation, 3), a sample holder, 4), an infrared detector, and 5) a computer to collect, process, and present the spectral data.

Patent Publication EP-0 557 655-A1 is disclosing a system for collecting weakly scattering optical signals (100) and employs a laser (102), which illuminates an unknown gas (107), contained by or within a long hollow chamber (105) having a highly reflecting coating (106 or 111).

The illuminating electromagnetic radiation (103) from the laser is directed along the entire length (L) of the chamber and collides with the vibrating molecules of the unknown gas within the containment tube.

The collisions causes the emission of shifted electromagnetic radiation (112) that is separated from the incident light and than is collected through one of the apertures (108) of the tube.

The scattered photons are than guided to a collection optics assembly (116), and a photodetector (124).

Patent Publication US-2006/119 851-A1 discloses a method and a device for measuring a concentration of a preselected gas in a gas sample.

The device comprises a "Harriott"-type multipass cell (10) having a center axis (74) and a housing (80A, 80B) surrounding and spaced from the axel to provide a tubular sample cavity (84).

The gas sample is pumped through the sample cavity via apertures (154, 156) provided in opposed ends of the axle.

A first mirror (44) and a second mirror (46) are supported at opposed ends of the axle.

A light source, e.g. a laser or LED, is provided for emitting a light beam into the sample cavity via an entry aperture (30) in the first mirror, the light beam having a wave length, at which the preselected gas strongly absorbs.

The beam is reflected between the mirrors for a number of times before exiting the cell via an exit aperture (48) in the second mirror and impinging on a detector (52).

The device further comprises a reference detector /32) for minitoring the intentensity of the unattenuated light beam and a detector for detecting the intensity of light transmitted through the second mirror after a single pass through the cell.

CONSIDERATION OF THE PRESENT INVENTION

Technical Problem

If the circumstance is considered, that the technical considerations which a person skilled in the relevant art of technology must carry out in order to offer a solution to one or more given technical problems are on the one hand initially a necessary understanding of the measures and/or the sequence of measures which are to be carried out and on the other hand a necessary choice of the one or more means, which are required, the following technical problems should in consideration of this be relevant in producing and forming the present subject of invention.

Considering the standpoint of earlier technology, as it has been described above, it should therefore be seen as a technical problem to be able to understand the significance of, the advantages related to and/or the technical measures and considerations which will be required to offer, in an arrangement adapted for spectral analysis, a simple and cost-effective way of having the intensity of electromagnetic radiations or light radiations analyzed, for analyzing a sample of a gas and/or a gas mixture, such as a sample having a relatively high concentration of gas, within a delimited space or cavity related to the measuring cell and its measuring distance.

There is a technical problem in being able to understand the significance of, the advantages related to and/or the technical measures and considerations that will be required for creating the prerequisites which are necessary for in reality being able to achieve high measuring accuracy, primarily by reducing the length of the measuring distance and reducing the overall size of the measuring cell with regard to its casing, such as one or more of the conditions disclosed under sections "i" to "n" above.

There is a technical problem in being able to understand the significance of, the advantages related to and/or the technical measures and considerations that will be required for creating prerequisites for reducing the effect of indirect radiation heat, emanating from a utilized absorption filter.

There is a technical problem in being able to understand the significance of, the advantages related to and/or the technical measures and considerations that will be required for letting the length of said measuring distance, between the transmitting means and the sensing means or detector, be selected to be very short, such as less than 15 millimeters, and having a narrow slit or aperture for passing light rays for passing generated light rays over the transmitting means be adapted such as to pass solely, or at any rate mainly, the light rays that are directed straight from the transmitting means and towards the sensing means or detector.

There is a technical problem in being able to understand the significance of, the advantages related to and/or the technical measures and considerations that will be required for letting the length of the measuring distance be chosen to solely between 1 and 6 millimeters, such as around 2-4 millimeters.

There is a technical problem in being able to understand the significance of, the advantages related to and/or the technical measures and considerations that will be required for letting said slit or aperture be adapted so narrow and/or limited that a light generating portion, associated with the transmitting means, will be able to project towards a light-receiving or light-sensitive portion, such as a chip, associated with the sensing means.

There is a technical problem in being able to understand the significance of, the advantages related to and/or the technical measures and considerations that will be required for letting said slit or aperture be allotted a limited dimension such, that it will cause the light-generating portion, such as a pinhole camera, to be projected against the light-receiving and light-sensitive portion or area.

There is a technical problem in being able to understand the significance of, the advantages related to and/or the technical measures and considerations that will be required for letting said sensing means, or in connection with said sensing means, be disposed adjacently to or close to one or more optical filters.

There is a technical problem in being able to understand the significance of, the advantages related to and/or the technical measures and considerations that will be required for letting said optical filter be subdivided into two partial portions so as by means of these to permit passage of mutually separated wavelength components or spectral elements and that to said receiving means this light-receiving or light-sensitive portion is to be shaped as two portions, with a first portion adapted to a first wavelength component and a second portion adapted to a second wavelength component.

There is a technical problem in being able to understand the significance of, the advantages related to and/or the technical measures and considerations that will be required for letting the transmitting means and the attachment bases, associated with the sensing means, be oriented in a right angle or at least an essentially right angle to the casing of the measuring cell and cavity.

There is a technical problem in being able to understand the significance of, the advantages related to and/or the technical measures and considerations that will be required for letting said slit or aperture be fashioned as two portions, with a first portion being adapted for a first wavelength component and a second portion being adapted for a second wavelength component.

There is a technical problem in being able to understand the significance of, the advantages related to and/or the technical measures and considerations that will be required for letting the attachment mountings of the transmitting means and the sensing means be oriented to the casing of the measuring cell and the cavity in a right or at any rate essentially right angle.

There is a technical problem in being able to understand the significance of, the advantages related to and/or the technical measures and considerations that will be required for letting said slit or aperture be fashioned in a disc or as an integrated wall portion of the cavity oriented, relatedly to the direction of the light rays, adjacently to or closely to but at a small distance from said sensing means and an optical filter related to this sensing means.

There is a technical problem in being able to understand the significance of, the advantages related to and/or the technical measures and considerations that will be required for letting said sample of gas in said cavity or measuring cell consist of a flowing gas, with said gas being adapted to pass, by said disc and/or wall portion, adjacently to said optical filter.

There is a technical problem in being able to understand the significance of, the advantages related to and/or the technical measures and considerations that will be required for letting said cavity or measuring cell and its surrounding wall portions in the measuring cell be processed and/or consist of a light-absorbing surface layer.

There is a technical problem in being able to understand the significance of, the advantages related to and/or the technical measures and considerations that will be required for letting the cavity of the measuring cell be restricted by a solidly related but easily removable wall portion or a cover.

There is a technical problem in being able to understand the significance of, the advantages related to and/or the technical measures and considerations that will be required for letting the wall portion or the cover of the measuring cell be adapted to cooperate with the remainder of the measuring cell by means of a gasket, such as an elastic "O"-ring or the like.

There is a technical problem in being able to understand the significance of, the advantages related to and/or the technical measures and considerations that will be required for letting the wall portion or cover have the form of a gas-penetrable filter for diffusion of the sample of gas intended for the measuring sequence.

There is a technical problem in being able to understand the significance of, the advantages related to and/or the technical measures and considerations that will be required for letting the wall portion or cover exhibit an inlet port or an outlet port for said sample of gas in the measuring cell and/or its cavity.

There is a technical problem in being able to understand the significance of, the advantages related to and/or the technical measures and considerations that will be required for letting the sample of gas be adapted to be supplied and removed at an overpressure, for increasing the concentration rate.

There is a technical problem in being able to understand the significance of, the advantages related to and/or the technical measures and considerations that will be required for letting a first portion of light rays be directed straight from the transmitting means towards the sensing means and a second portion of light rays be directed reflected towards the sensing means for individual light-receiving portions.

There is a technical problem in being able to understand the significance of, the advantages related to and/or the technical measures and considerations that will be required for having a performed measuring modified with an external partial system adapted for compressing the measuring gas modified so as to thereby create a more distinct weakening of the amplitude with the increased concentration.

There is a technical problem in being able to understand the significance of, the advantages related to and/or the technical measures and considerations that will be required for being able to and letting the amplification factor be limited in the absorption calculations so as to thereby be able to limit the influence of a noise factor.

There is a technical problem in being able to understand the significance of, the advantages related to and/or the technical measures and considerations that will be required for creating prerequisites for elucidating a zero-point and/or a zero-point error.

There is a technical problem in being able to understand the significance of, the advantages related to and/or the technical measures and considerations that will be required for building on an arrangement, with a transmitting means adapted for electromagnetic radiation, a space in the form of a cavity surrounding and enclosing the sample of gas and serving as a measuring cell with its measuring path and being intended to be able to define an optical measuring distance through the sample of gas; a sensing means in the form of a detector for said electromagnetic radiation, which passes through said optical measuring distance from said transmitting means; and at least one unit performing the spectral analysis and being connected to said sensing means, wherein said means sensing the electromagnetic radiation is adaptedly opto-electrically sensitive to the electromagnetic radiation, which is intended to fall within (the wavelength component or) the spectral region whose chosen spectral element(s) is to become the subject of an analysis in the unit performing the spectral analysis so as to determine, within this unit, the (relative) radiation intensity of the spectral element(s) and to present the latter on a display unit or screen or corresponding means, wherein it is possible in simple manner and cost-effectively to be able to spectrally analyse the intensity, in terms of wavelength, of closely adjacent lying components or spectral elements of a combined light or electromagnetic light bundle of different wavelengths at high concentrations of gas.

There is a technical problem in being able to understand the significance of, the advantages related to and/or the technical measures and considerations that will be required for, with the prerequisites given above, measuring the mutual relationship of signal intensities with regard to each other and solely for specific and closely related wavelength components and/or spectral elements.

There is a technical problem in being able to understand the significance of, the advantages related to and/or the technical measures and considerations that will be required for letting a limited spectral analysis be adapted to a measuring technology within measuring of gas analysis and gas concentration, in which a specific "spectral signature" or a "signal depression or inpression" is required for letting these be the bases of a matter-unique identification and/or determination of contents, at least in a high concentration of gas and of a short measuring distance, such as around 3 millimeters.

There is a technical problem in being able to understand the significance of, the advantages related to and/or the technical measures and considerations that will be required for letting a small number of wavelength-specific measuring points or spectral elements, but with at least one wavelength point per matter, become the object of an identification and/or a supervision.

There is a technical problem in being able to understand the significance of, the advantages related to and/or the technical measures and considerations that will be required for utilizing electromagnetic bandpass filters for being able to create measuring signals at fixed predetermined wavelengths in accordance with the principles of a non-dispersive infrared technology (Non-Dispersive InfraRed or "NDIR"-technique).

There is a technical problem in being able to understand the significance of, the advantages related to and/or the technical measures and considerations that will be required for letting said sample of gas in said measuring chamber be subjected to an overpressure chosen beforehand.

There is a technical problem in being able to understand the significance of, the advantages related to and/or the technical measures and considerations that will be required for having a delivered result, depending on one or more wavelengths during absorption in the measuring cell or measuring chamber, be compensated, over an adapted correction circuit, for an influence of the chosen overpressure and a chosen gas or mixture of gases, for delivering a signal corresponding to the concentration of the relevant gas or gas mixture at atmospheric pressure.

There is a technical problem in being able to understand the significance of, the advantages related to and/or the technical measures and considerations that will be required for letting the overpressure chosen beforehand be capable of being generated by a mechanical means.

There is a technical problem in being able to understand the significance of, the advantages related to and/or the technical measures and considerations that will be required for letting the mechanical means comprise a piston-cylinder arrangement, whose piston is displaceably disposed between associated turning points in a cylinder unit.

There is a technical problem in being able to understand the significance of, the advantages related to and/or the technical measures and considerations that will be required for having said electromagnetic radiation be adapted to pass a specifically adapted optical bandpass filter, places between said transmitting means and said sensing means.

There is a technical problem in being able to understand the significance of, the advantages related to and/or the technical measures and considerations that will be required for letting such bandpass filter be structured or constructed such as to be capable of offering in the transmission a wavelength dependent on the angle of incidence of the electromagnetic radiation, with a large wave range generated and transmitted in said transmitting means.

There is a technical problem in being able to understand the significance of, the advantages related to and/or the technical measures and considerations that will be required for letting this bandpass filter then, by means of its structure and by chosen angles of incidence or similar, be adapted to separate a first chosen spectral element(s) and/or a first wavelength component from a second chosen spectral element and/or a second wavelength component(s) in one and the same transmitted electromagnetic radiation.

There is a technical problem in being able to understand the significance of, the advantages related to and/or the technical measures and considerations that will be required for letting said unit be adapted to be able to electrically detect via optoelectric detectors an occurring radiation intensity applicable to more than one wavelength component and/or more than one spectral element.

There is a technical problem in being able to understand the significance of, the advantages related to and/or the technical measures and considerations that will be required for letting the optical (electromagnetic) bandpass filter be adapted to be able to deflect an incident and emitted optical or electromagnetic radiation to at least two different optical and predetermined outfalling or outgoing angles, each one applicable to a narrow wavelength component(s) and/or spectral element(s).

There is a technical problem in being able to understand the significance of, the advantages related to and/or the technical measures and considerations that will be required for each or for each chosen outfalling or outgoing angle of the radiations indicating the existence of an opto-electric detector, which is adapted to analyse its electrically associated wavelength component(s) or its associated spectral element(s) in its associated unit performing the spectral analysis.

There is a technical problem in being able to understand the significance of, the advantages related to and/or the technical measures and considerations that will be required for selecting a filter active on the basis of optical interference as said optical bandpass filter.

There is a technical problem in being able to understand the significance of, the advantages related to and/or the technical measures and considerations that will be required for determining an instantaneously occurring concentration, such as of carbon dioxide ($CO_2$).

The Solution

This invention takes as its starting point the known technology indicated by way of introduction and is based on an arrangement adapted for a spectral analysis of gas concentrations having a means, adapted for transmitting electromagnetic radiation in accordance with the preamble of claim 1.

In addition to the mentioned transmitting means the arrangement utilized here is for gas test analysing also to indicate a space, such as in the form of a cavity, serving as a measuring cell intended for the sample of gas and being intended to be able to define an optical measuring distance, a sensing means or detector of said electromagnetic radiation passing said optical measuring distance from said transmitting means, and a unit performing spectral analysis and being connected at any rate to said sensing means, wherein said means or detector, sensing the electromagnetic radiation, is adapted to be sensitive of the electromagnetic radiation, which is intended to fall in the spectral range whose chosen wavelength component(s) and/or spectral element(s) i.a. over an optical filter, which is to be the subject of analysis in the unit performing the spectral analysis, so as within this unit being able to determine the relative intensity of radiation of the wavelength component(s) or the spectral elements) in relation to a relatively high concentration of gas.

In order to be able to solve one or more of the technical problems mentioned above the present invention more specifically indicates that the thus known technology is to be supplemented by letting the length of said measuring distance, between the transmitting means and the sensing means or detector, be chosen to be short, such as to less than 15 millimeters, and that a narrow slit or aperture for passing light rays, is passing light rays over the transmitting medium, and is adapted such, that it lets through solely or at any rate mainly, those light rays which are directly directed from the transmitting means towards the sensing means or detector.

As proposed embodiments falling within the frame of the present inventive concept it is indicated that the length of the measuring distance in reality should be chosen to between 1 and 6 millimeters, such as around 2-4 millimeters.

Said slit or aperture is then to be adapted so narrow or restricted that a light generating portion, associated with the transmitting means, will be able to project against a light-receiving or light-sensitive portion or area allotted to the sensing means, such as a chip.

Said slit or aperture is then to be allotted a limited dimension that causes the light-generating portion, such as a pinhole camera, to be able to be projected towards the light-receiving portion or area.

Said optical filter is adapted adjacent to said sensing means or in connection with said sensing means.

Said optical filter can be subdivided into two parts for permitting, by means thereof, mutually different wavelength components or spectral elements to pass, with said receiving means and these light-receiving or light-sensitive parts being shaped as to two parts, with one part adapted to a first wavelength component and a second portion adapted to a second wave-length component.

Mountings for the transmitting means and the sensing means should be, with regard to the casing of the measuring cell and the cavity, oriented at a right angle or at least an essentially right angle.

Said slit or aperture is fashioned in a disc or a wall portion oriented, related in the direction of the light rays, adjacent to but a small distance from said sensing means and an optical filter, related to this sensing means.

Said cavity or measuring cell and its surrounding wall portions in the measuring cell are processed and/or consist of a layer absorbing light rays.

The cavity of said measuring cell is proposed to be limited by a solidly related, but easily removable, wall portion or a cover.

The wall portion or the cover of the measuring cell is adapted to cooperate with the measuring cell in general over a gasket, such as an elastic "O"-ring.

The wall portion or cover is allotted the form of a gas-permeable filter, for creating prerequisites for a diffusion of the sample of gas or gas mixture.

The wall portion or cover exhibits an inlet port and/or an outlet port for said sample of gas in the cavity.

The sample of gas is adapted to be able to be supplied under a predetermined overpressure.

A first portion of light rays is directed directly from the transmitting means and towards the sensing means, and a second portion of light rays is directed reflected towards the sensing means for individual light-receiving portions.

Furthermore, it is indicated that said gas in the mentioned measuring chamber can be subjected to an overpressure chosen in advance and wherein a delivered result, depending on one or more wavelengths being absorbed in the measuring chamber, is compensated for over a correction circuit relevant for the chosen overpressure with regard to the atmospheric pressure.

As proposed embodiments falling within the framework of the present invention it is additionally indicated that the overpressure is to be adapted and chosen in response to the capability of absorption existing at the chosen overpressure for a chosen gas and/or gas mixture.

The correction circuit cooperates with a correction unit having an ability of absorption/pressure relation for a circuit determining a chosen gas or gas mixture.

The overpressure chosen beforehand may be generated by a mechanical means, with said means being comprised of an arrangement of piston and cylinder, said piston being movably disposed between associated turning points and alternatively having the mechanical means comprise a magnetic body, oriented in the measuring cell, said body being capable of carrying out an oscillating motion by a surrounding electric circuit.

In accordance with the present invention it is further indicated that said transmitted electromagnetic radiation, between said transmitting means and said sensing means, can be adapted to pass a frequency and/or wavelength-adapted optical bandpass filter, with said bandpass filter being structured and/or designed for being able to offer a wavelength dependent of the angle of incidence in the transmission of the electromagnetic radiation generated by said transmitting means.

This bandpass filter is then adapted to wavelengths separating a first chosen wavelength component(s) or a narrow area or a first chosen spectral element(s) from a second chosen wavelength component(s) or a narrow area or a second chosen spectral element(s) within the transmitted electromagnetic radiation, and said unit is adapted for being able to detect, by means of one or more opto-electrical detectors, occurring intensities of radiation from one or from more than one such spectral element.

The optical bandpass filter is here adapted for letting incident electromagnetic radiation be deflected in at least two predetermined outfalling or outgoing angles of the electromagnetic radiations.

More particularly it is indicated that one and the same bandpass filter is to be adapted to receive one and the same electromagnetic radiation, within which radiation in any case two different wavelength components or spectral elements fall.

As said optical bandpass filter may to advantage be chosen a filter, active on the basis of optical interference.

Within the framework of the invention evaluation of the existence of and the concentration of carbon dioxide ($CO_2$), such as in air or exhalation air, are included.

A light ray (in the form of a narrow electromagnetic bundle of radiation) or a selected portion of light rays may to advantage be adapted to be directly directed at a right angle towards an opto-electric detector from a transmitting means.

Advantages

The advantages which primarily must be considered as being characterizing of the present invention and the specific significative characteristics indicated thereby are that hereby prerequisites have been created for an arrangement adapted for spectral analysis having a transmitting means adapted for electromagnetic radiation, a space, and a sensing means or detector of said electromagnetic radiation from said transmitting means, and a unit performing the spectral analysis at any rate connected to said sensing means, wherein the mentioned means (or detector) sensing the electromagnetic radiation is to be adaptedly sensitive to the filter-passing electromagnetic radiation which is intended to fall within the spectral field whose chosen wavelength component(s) or spectral element(s) are over an optical filter to become objects of an analysis in the unit performing the spectral analysis for determining in this unit, by various calculations, the relative radiation intensity of the spectral element(s) for high concentrations of gas, indicating that the length of said measuring distance between the transmitting means and the sensing means or detector is to be chosen to be short, such as to less than 15 millimeters.

A narrow slit or aperture letting through light rays in the form of generated light rays via the transmitting means is to be adapted such, that it lets through solely or at least mainly the light rays which are directed directly from the transmitting means and towards the sensing means or detectors.

The length of the measuring distance is preferably to be chosen at between 1 and 6 millimeters, such as around 2-4 millimeters.

The subject matter, which primarily must be considered to be characterizing of the present invention, is disclosed in the characterizing portion of the following claim 1.

SHORT DESCRIPTION OF THE DRAWINGS

A presently proposed embodiment, exhibiting the significative characteristics related to the present invention, will now be described more specifically as an example with reference to the accompanying drawings, in which;

FIG. 1 shows the principle of measuring gas at high gas concentrations while utilizing a NDIR-technology with a light transmitting means, a space adapted for a gas test, such as a cavity in a measuring cell, a light sensing means or detector and a light calculating unit, adapted to performing a spectral analysis and its associated display unit or the like, as well as a correction circuit, compensating for the absorption capability in dependency of prevailing pressure.

FIG. 2 shows in an enlarged scale the means transmitting light rays and the means for sensing light rays or detector with a measuring distance "L" therebetween and in a first embodiment.

FIG. 3 illustrates in this respect a second embodiment.

FIG. 4 illustrates a third embodiment with directly acting light rays and indirectly or reflected acting light rays.

Figure 5:
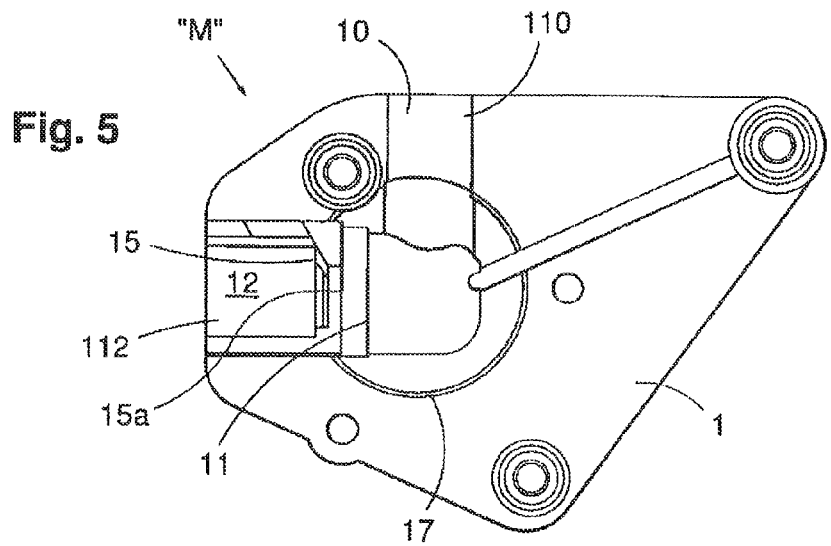
FIG. 5 shows a plan view of a measuring cell, with a casing and cavity and with openings for the transmitting means' and the sensing means' mountings.
Figure 6:
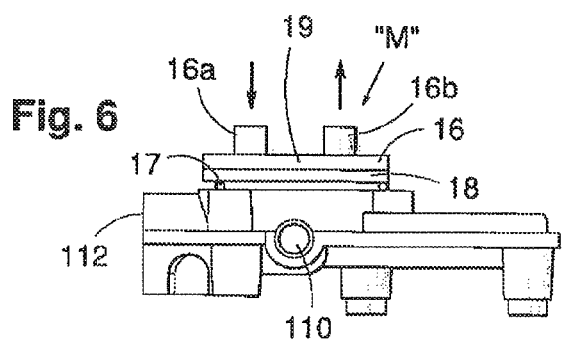
Figure 7:
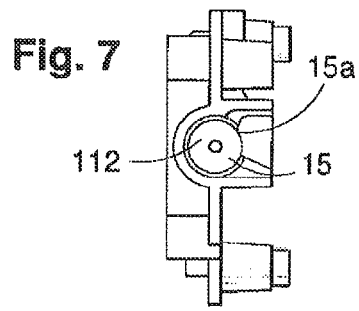
Figure 8:
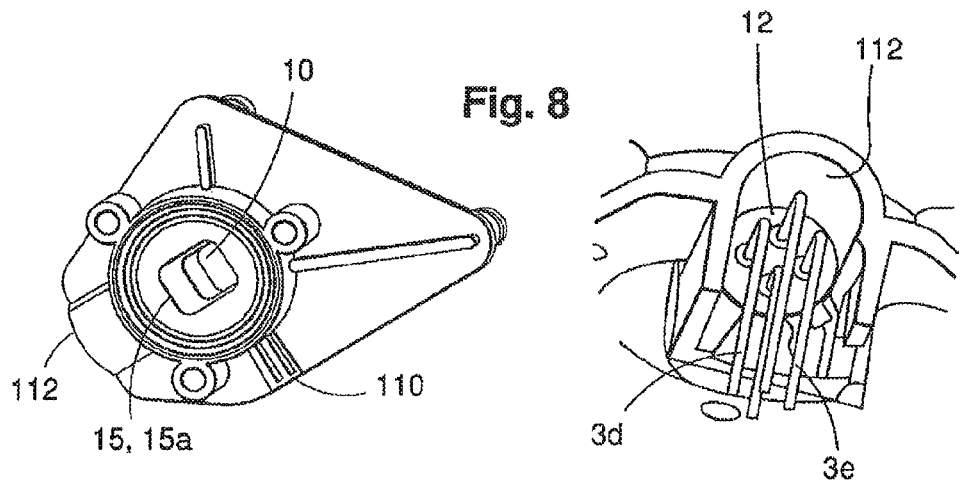

FIG. 6 shows FIG. 5 in a lateral view, with a wall portion or a cover with an inlet port and an outlet port for a gas-permeable filter, FIG. 7 shows FIG. 5 in another lateral view of the measuring cell, and FIG. 8 shows the measuring cell, according to FIGS. 5 to 7, in two different perspective views, one corresponding to the illustration in FIG. 5 the other disclosing an enlarged under section of said measuring cell.

DESCRIPTION OF THE PRESENTLY PROPOSED EMBODIMENT

By way of introduction it should be pointed out that in the following description of a presently proposed embodiment which exhibits the significative characteristics related to the invention and which is clarified by the Figures, shown in the accompanying drawings, we have chosen terms and specific terminology with the purpose of thereby primarily clarifying the basic concept of the invention.

However, in this connection it should be noted that the terms chosen here are not to be seen as limiting solely to the terms utilized and chosen here and it should be understood that each term chosen in this manner is to be interpreted such, that in addition it will be capable of comprising all technical equivalents which function in the same manner or essentially the same manner so as to thereby result in achieving the same or essentially the same purpose and/or technical effect.

Thus, with reference to the accompanying drawings, the basic prerequisites for the present invention are shown schematically and in detail, with the significative peculiarities or features associated with the invention being concretized by the embodiments now proposed and more specifically described in the following.

Thus, FIG. 1 schematically shows the principle of an arrangement "A" adapted for spectral analysis with a light transmitting means 10 adapted for an electromagnetic radiation "S" with a large wave range and a delimited space 11, in the form of a cavity, serving as a measuring cell 1 adapted for a sample "G" of gas and intended to be able to define an optical measuring distance, designated "L" (See FIG. 2).

Furthermore, a light sensing means 12 or detector (3b) of said electromagnetic radiation "S", passing said optical measuring distance "L" from said light transmitting means 10 and a unit 13 performing the spectral analysis connected over a lead 121 to at least said sensing means 12 and therein included opto-electric detectors are illustrated.

Also, the means 12 sensing the electromagnetic radiation "S" should be mentioned, and the thereto belonging detector and/or detectors 3b should be adapted to be sensitive to the electromagnetic radiations, which are intended to fall within the spectral field whose chosen wavelength component(s) or spectral element(s) are to become objects of analysis within the unit 13 performing the spectral analysis so as to primarily having calculated and determining the relative intensity of radiation of a chosen spectral element in this unit 13.

Said transmitted electromagnetic radiation "5", between said transmitting means 10 and said sensing means 12 is adapted to pass towards and to selectively pass through a bandpass filter, such as an optical bandpass filter 14 (See FIG. 2).

Such bandpass filter 14:3 is, according to FIG. 4, structured and/or designed so as to offer a wavelength dependent of the angle of incidence in the transmission of the electromagnetic radiation "Sa1" and "Sa2" generated by said transmitting means 10.

This bandpass filter 14:3 in FIG. 4 is adapted to separate, with a chosen angle of incidence, a first chosen spectral element 4a from a second chosen spectral element 4b, and two opto-electric detectors 3b and 3b' are both connected to said unit 13, which is adapted with modules for detecting an occurring radiation intensity for more than one such spectral element.

The unit 13 performing the spectral analysis exhibits a transmitter module 13a for electromagnetic radiation "S" or "Sa" over a line 101 and controlled and activated by a central unit 13b, and a number of signal receiving modules 13c, 13d and 13e, serving as detectors, are also connected to central unit 13b.

Over a circuit 13g signals emanating from electromagnetic radiation "Sa" can be compared to a received selective electromagnetic radiation "Sb" (4a, 4b) in unit 13 over the transmitting means 10.

The evaluated and calculated result in the central unit 13b can then be transferred to a computer 20 having a display unit 20a, as a graph 20a' or similar over a circuit 13k.

More specifically, FIG. 1 illustrates an application in an absorption cuvette, in which cuvette the sample "G" of gas, which with the assistance of the electromagnetic radiation "Sa", or considered as a bundle of radiation, is to be analyzed, with the radiation "S" resp. "Sa" being transmitted by an emitter unit 10 and being received by opto-electric detectors, such as a detector 3b.

This emitter unit 10 can then consist of a source of radiation and a collimator coordinating rays of light with the purpose of gathering, as effectively as possible, the emitted radiation "Sa" with its bundle of radiation and directing the same through the length of the absorption cuvette towards the detector 12 or 3b.

Emitter unit 10 can here have the form of a glowing wire in a glass bulb filled with gas or evacuated of gas, i.e. an incandescent lamp, or a heated resistor on a ceramic substrate or on a thin membrane produced by silicon technology and micromechanics or a light-emitting diode, having a well defined emission spectrum.

In accordance with the instructions of the invention the emitter unit 10 is to transmit an emission "S" and "Sa" of bundles of radiation, which at least must comprise all of the wavelengths whose intensities are to be detected opto-electrically in their detector 3b or in individual detectors 3b, 3b' and be evaluated in unit 13.

The absorption cuvette can then be designed in different ways depending on the chosen application, chosen measuring accuracy, the manner in which the measuring gas or sample "G" of gas can be expected to be collected, via overpressure, etc.

In certain applications the space 11 of the absorption cuvette 1 can concurrently be permitted to be the mechanical body on which the emitter unit 10 and the receiver 12 are solidly mounted.

The detector 3b of the receiver unit or means 12 is adapted to create the opto-electric wavelength-dependent electrical signals, which later are to become the object of a calculating analysis in the unit 13 performing the spectral analysis.

Such units 13 are well known in this technical field and are therefore not described in detail.

Said unit 13 is intended to calculate the result, which discloses a relevant concentration of gas and/or a gas and/or a gas mixture.

It is important that the opto-electric detector 3b has the ability of generating some kind or some form of electric signals, whose size and shape are to be dependent of and correspond to the intensity of radiation 4a passing through an opening or aperture 15a and filter 14 with its frequency range.

By means of not shown electric connections these electric signals are transferred to the two measuring legs 3d and 3e of the receiver unit or means 12, from where a subsequent amplifier stage (not shown) in unit 13 and/or other electronics/computer processing refines the measuring signal to a final result, which may be evaluated, for example visible as a graph 20a' on display unit 20a.

If measuring of gas is to occur according to NDIR-technology the wavelength for the filter transmission 4a is chosen to coincide with an absorption wavelength, which is characteristic of the matter whose concentration of gas is to be measured.

Short-time variations in the inwardly radiated intensity from the electromagnetic radiation "S" or the light clusters or rays "Sa", which run the risk of distorting a careful evaluation of the measuring signals on lead 121, can be neutralized and regulated away entirely if one of the measuring channels is used as an intensity reference over a signal neutral wavelength.

With reference to FIG. 6, more specifically an arrangement "M" for compressing the sample "G" of gas and for increasing the value of the evaluating concentration of gas to values that may be more carefully evaluated is illustrated.

The invention is to be exemplified with high values of gas concentration either occurring naturally or in a gas compressed form.

Correction circuit 13g is only schematically indicated but cooperates with a correction unit 13h, with a circuit determining capability of absorption/pressure for each gas or gas mixture and wherein the relationship of the absorption capacity to the chosen pressure can be illustrated in a "Pa"-graph (Pressure-Correction-Graph).

Thus, correction circuit 13g is adapted to reduce an evaluated fictive gas concentration with a stored or evaluated value.

The overpressure (Pa) chosen beforehand may be generated by a mechanical means or an arrangement, not illustrated.

The mechanical means can consist of a piston-cylinder-arrangement, the piston of which is displaceably positioned between associated turning points.

The mechanical means can consist of a magnetic body oriented in measuring cell 11 or related to the measuring cell, with said body being capable of being given an oscillating motion by a surrounding electric circuit (not shown).

The frequency of a chosen change of overpressure via means can be chosen to between 1 and 50 Hertz, such as around 25-35 Hertz.

The measuring chamber 11 can be adapted to a volume of 0.5 to 3.0 cubic centimeters, such as around 0.8-1.2 cubic centimeters.

The increase of pressure is dependent on an expected concentration of gas and should in the normal case be chosen to between 1:2 and 1:10, such as around 1:4 to 1:6.

The correction circuit 13g is adapted to produce a reduced value of the gas concentration to the display unit 15 related to the atmospheric pressure.

Thus, there is a number of possible solutions of the arrangement "A" and variations thereof which on the one hand can generate the necessary angles of incidence of the receiver unit 12 and on the other hand can assign other means for generating different pressures and different correction circuits 13g so as thereby to offer solutions of the arrangement "A" associated with the invention.

With a specific description of the present invention as it may be seen in FIG. 1 measuring of high concentrations of gas will be particularly accentuated.

Thus, FIG. 2 (enlarged view) illustrates that the length "L" of said measuring distance between the transmitting means 10 and the sensing means 12 or the detector 3b has been chosen to be short, such as to less than 15 millimeters.

A narrow slit or aperture 15a, letting through generated light rays via the transmitting means 10, is adapted such, that it will let through solely or at least mainly the light rays "Sa", which are directed straight from the transmitting means 10 and towards the sensing means 12 or its detectors 3b, 3b''.

The length of the measuring distance is in reality to be chosen to be as short as possible, such as to between 1 and 6 millimeters, such as around 2-4 millimeters.

The embodiment shows a length of approximately 3 millimeters.

Said slit or aperture 15a in a disc 15 is adapted to be so narrow and/or limited that a light generating portion 10a, "Sb", associated with the transmitting means 10, will be able to be projected towards a light receiving or light sensitive portion 12a, 3b associated with a sensing means 12, such as a sensing chip 3b, 3b'.

Furthermore, said slit or aperture 15a in a disc 15 is to be allotted such a limited dimension that makes the light generating portion 10a "Sb", such as a pinhole camera, able to be projected towards the light-receiving portion 12a, 3b.

FIGS. 2, 3 and 4, respectively, now illustrate that to said sensing means 12 or in connection with said sensing means 12 said optical filter is disposed, which is designated the reference numeral 14 in FIGS. 2, 14:1 and 14:2 in FIGS. 3 and 14:3 in FIG. 4.

Said optical filter 14 can thus be subdivided into two partial portions 14:1 and 14:2 so as by means of these to permit mutually separated wavelength components or spectral elements 4a' and 4b' (In FIG. 3) to pass, and than to said receiving means 12, the light-receiving or light-sensitive portion 12a thereof is formed as two portions 12a1 and 12a2, respectively, with one portion adapted to a first wavelength component and a second portion adapted to a second wave-length component.

Mounting bases or recesses 110, 112 (In FIG. 5) belonging to the transmitting means 10 (or receiving means 12) are oriented to a casing 1 of the measuring cell 11 and the cavity at a right angle or under all circumstances an essentially right angle, which FIG. 5 has the purpose of illustrating.

Said slit or aperture 15a is formed in a disc 15 or as a wall portion of the cavity oriented, related to the direction of the light rays, adjacent to but at a small distance from said sensing means 12 and an optical filter 14 related to said sensing means.

Said sample "G" of gas in said cavity or measuring cell 11 consists of a flowing gas, wherein the sample of gas is adapted to pass along said disc 15 and said optical filter 14.

More specifically it is indicated that said cavity 11 or measuring cell 1 and its surrounding wall portions in the measuring cell are processed and/or consist of a light-absorbing layer.

However, the cavity of the measuring cell is limited by a solidly related but easily removable wall portion or a cover 16.

The wall portion or cover 16 of the measuring cell 1 is adapted to cooperate with the remainder of the measuring cell via a gasket, such as an elastic "O"-ring 17.

The wall portion or cover 16 can be allotted the form of supporting a gas-penetrable filter 18 for diffusion of the sample of gas.

The wall portion or cover 16 exhibits an inlet port 16a and/or an outlet port 16b for said sample "G" of gas within cavity 11.

Thus, FIG. 4 illustrates that a first portion of light rays "Sa1" is directed straight from the transmitting means 10 and towards the sensing means 3b' and that a second portion of light rays "Sa2" is directed reflectingly in a mirror surface 19 towards the sensing means 3b for each individual light-receiving portion.

With reference to FIG. 8 certain parts and details of the arrangement are shown and illustrated in a 3-dimensional design.

Thus, this invention intends to be able to offer an evaluation of high concentrations of a gas included in a mixture comprising one or more gases.

With regard to $CO_2$-gas it has turned out to be possible to detect and determine a concentration of 5% and higher, such as 6-30%, in measuring exhaust gases.

For methane gas an evaluation of a gas concentration between 0-4 volume percentage is proposed. In a LEL system (Lower Explosive Limit) this is mentioned as between 0 and 100%. Thus, this is relevant to a gas burners.

If the embodiment described above is considered it should be noted that the embodiment of FIG. 2 very well can be supplemented with two or more parallel bundles of light, each one associated with its slit or aperture, with individual optical filters adapted for one and the same or different frequency ranges.

Although the embodiments illustrate a small separation between disc 15 or the wall portion it lies within the scope of the invention to glue an optical filter to the detector and to glue a cover to this detector, having a slit or an aperture 15a adjacent to the light-sensitive chip.

However, FIGS. 5 to 8, respectively, illustrate that a wall portion 15 of the cavity 11 is provided with a slit or an aperture 15a and that the detector with the optical filter is introduced as a unit, so as to engage or to be positioned at a small distance from the slit or aperture 15a.

In FIG. 6 the cover 16 can be replaced by a diffusion filter (19) for letting a surrounding gas diffuse into the cavity of measuring cell 1.

Here, the cover 16 is easily removable and easily positionable such as a slanting wall portion of the measuring cell 1.

The invention is of course not limited to the embodiment disclosed above as an example, and it can be subjected to modifications within the frame of the inventive concept, which is illustrated in the following claims.

It should be particularly noted that each illustrated unit and/or circuit can be combined with each other illustrated unit and/or circuit within the scope of being able to achieve the desired technical function.

The invention claimed is:

1. A device adapted for spectral analysis of high concentrations of gas, the device comprising:
    a light emitting means configured to generate electromagnetic radiation;
    a gas-adapted measuring cell defining an optical measuring distance;
    a detector configured to detect the electromagnetic radiation passing through the optical measuring distance from the light emitting means; and
    an analysis unit configured to perform the spectral analysis and being connected at least to the detector,
    wherein the detector is opto-electrically sensitive to the electromagnetic radiation, the electromagnetic radiation falling within a spectral area whose chosen wavelength components are passed through an optical filter to become objects of an analysis in the analysis unit performing the spectral analysis for determining the intensity of radiation of the wavelength components,
    wherein a length of the optical measuring distance between the light emitting means and the detector is less than 15 millimeters, and that a plate having an aperture is arranged between the light emitting means and the detector such that electromagnetic radiation from the light source directly impinges the detector.

2. The device in accordance with claim 1, wherein the length of the measuring distance is chosen to between 1 and 6 millimeters.

3. The device in accordance with claim 1, wherein the aperture is allotted a dimension such that the aperture makes a light-generating portion be projected towards a light-receiving area.

4. The device in accordance with claim 1, wherein the detector is arranged with the optical filter.

5. The device in accordance with claim 1, wherein the optical filter is subdivided into two partial portions that allow a passage of mutually different wavelength components, and at least one of a light receiving portion and light sensitive portion of the detector is formed as the two partial portions, with a first portion adapted for a first wavelength component and a second portion adapted for a second wavelength component.

6. The device in accordance with claim 1, wherein the plate with the aperture is provided as a wall portion for the measuring cell and is oriented, relatedly to the direction of the electromagnetic radiation, adjacently to but at a short distance from the detector and the optical filter.

7. The device in accordance with claim 1, wherein the measuring cell and surrounding wall portions of the measuring cell are processed or includes a light-absorbing surface layer, or are processed and includes a light-absorbing surface layer.

8. The device in accordance with claim 1, wherein a cavity formed by the measuring cell is limited by a solidly related but easily removable wall portion.

9. The device in accordance with claim 8, wherein the wall portion of the measuring cell is configured to cooperate with a remainder of the measuring cell via a gasket.

10. The device in accordance with claim 8, wherein the wall portion includes a gas-permeable filter.

11. The device in accordance with claim 8, wherein the wall portion includes at least one of an inlet port and an outlet port for a sample of gas in the cavity.

12. The device in accordance with claim 1, wherein a first portion of electromagnetic radiation is directed directly from the light emitting means and towards the detector, and a second portion of electromagnetic radiation is directed reflected towards the detector for individual and separated light-receiving portions.

13. The device in accordance with claim 12, wherein the second portion is reflected in a mirroring portion.

14. The device in accordance with claim 1, wherein the electromagnetic radiation between the light emitting means and the detector is configured to pass an optical bandpass filter, the optical bandpass filter is configured to provide a wavelength dependent of an angle of incidence for the transmission of the electromagnetic radiation generated by the light emitting means, with the optical bandpass filter configured to separate at least one of a first chosen wavelength component and a first chosen spectral element from at least one of a second chosen wavelength component and a second chosen spectral element for being received in an individual detector related portion and that the analysis unit is configured to detect and calculate an incident radiation intensity for more than one received wavelength component.

15. The device in accordance with claim 14, wherein the optical bandpass filter is configured to deflect, in response to a relevant angle of incidence, an incoming electromagnetic radiation in at least two different predetermined deflected angles.

16. The device in accordance with claim 15, wherein the optical bandpass filter includes a filter active on optical.

17. The device in accordance with claim 1, wherein a gas concentration of carbon dioxide ($CO_2$) is evaluated and is presented as a graph on a display unit.

* * * * *